United States Patent [19]

Weinberg et al.

[11] 4,361,540

[45] Nov. 30, 1982

[54] ANALYSIS SYSTEM

[75] Inventors: Melvin S. Weinberg, Nashua, N.H.; Alan D. Cormier, Newburyport, Mass.

[73] Assignee: Instrumentation Laboratory Inc., Lexington, Mass.

[21] Appl. No.: 319,314

[22] Filed: Nov. 9, 1981

Related U.S. Application Data

[63] Continuation of Ser. No. 146,705, May 5, 1980, abandoned.

[51] Int. Cl.³ .......................................... G01N 27/30
[52] U.S. Cl. .................................. 422/68; 204/195 B; 422/98
[58] Field of Search ....................... 422/68, 80, 81, 98, 422/61, 70; 23/928; 204/195 B, 195 F, 195 P

[56] References Cited

U.S. PATENT DOCUMENTS

| 3,522,725 | 8/1970 | Waters | 422/70 X |
|---|---|---|---|
| 3,640,267 | 2/1972 | Hurtig et al. | 422/68 |
| 3,648,159 | 3/1972 | Stansell et al. | 23/928 X |
| 3,672,843 | 6/1972 | Rosse et al. | 422/68 |
| 3,763,422 | 10/1973 | MacPhee et al. | 422/68 X |
| 3,811,841 | 5/1974 | Kassel | 422/81 |
| 3,811,842 | 5/1974 | Diebler et al. | 422/81 X |
| 3,884,640 | 5/1975 | Lock et al. | 422/68 |
| 3,960,498 | 6/1976 | Zindler et al. | 204/195 P X |
| 3,963,440 | 6/1976 | Stein et al. | 204/195 P X |
| 4,086,061 | 4/1978 | Hoffa et al. | 422/68 |
| 4,160,714 | 7/1979 | Andersen et al. | 204/195 P |
| 4,202,747 | 5/1980 | Buzza et al. | 204/195 P X |
| 4,207,394 | 6/1980 | Aldridge | 422/61 X |
| 4,221,567 | 9/1980 | Clark et al. | 23/230 B |

FOREIGN PATENT DOCUMENTS

| 2848073 | 5/1979 | Fed. Rep. of Germany | 23/928 |
|---|---|---|---|
| 1047138 | 11/1966 | United Kingdom . | |
| 1068661 | 5/1967 | United Kingdom . | |
| 1084079 | 9/1967 | United Kingdom . | |
| 1346533 | 2/1974 | United Kingdom . | |
| 1535361 | 12/1978 | United Kingdom . | |
| 1558818 | 1/1980 | United Kingdom . | |

Primary Examiner—Kenneth M. Schor

[57] ABSTRACT

An analysis system for measuring a plurality of parameters of a fluid sample comprises a housing, and a flow-through cell in the housing that has opposed surfaces with at least two ports in each surface. One of the ports is an inlet port, a second of the ports is an outlet port, and at least two of the ports are sensing ports. A sample flow path including a serpentine portion in the cell serially connects the ports and extends from a port in one surface to a port in the other surface and back to a port in the one surface, and a sensor is disposed in sealing engagement with each sensing port and forms a portion of the serpentine flow path so that sample fluid to be analyzed contacts a surface of each sensor.

18 Claims, 15 Drawing Figures

4,361,540

ANALYSIS SYSTEM

This is a continuation of application Ser. No. 146,705 filed May 5, 1980 now abandoned.

This invention relates to apparatus for the analysis of fluid samples and has particular application to apparatus for the analysis of parameters of precious fluids such as blood.

Frequently, an accurate measurement of two or more constituents of a fluid sample of small volume is desired. For example the values of particular constituents of a blood sample may be useful in providing diagnostic information or for the control of life support devices. In particular instances, pH, $pCO_2$, and $pO_2$ values of blood specimens provides important clinical information, and analysis systems employing electrochemical electrodes have been developed for such analysis. Examples of such blood analysis systems are shown in Spergel U.S. Pat. No. 3,658,478 and Zindler U.S. Pat. No. 3,960,498. In such systems, the fluid to be analyzed must be brought to and maintained at a desired stable measuring temperature as the measurement electrode systems in such systems are temperature sensitive. For example blood samples to be analyzed are frequently refrigerated. Exposure of electrode assemblies to different calibrating media or to different temperatures or to reference electrolyte materials may degrade the response of the sensing electrode.

In accordance with the invention there is provided a fluid analysis system that provides improved performance in terms of sample size, accuracy, and precision with a constant temperature environment for the measuring electrodes, sampling cuvette and ancillary components.

In accordance with one aspect of the invention, there is provided an analysis system for measuring a plurality of parameters of a fluid sample that comprises a housing, with a flow-through cell in the housing the flow-through cell having opposed surfaces with at least two ports in each surface. One of the ports is an inlet port, a second of the ports is an outlet port, and at least two of the ports are sensing ports. A sample flow path includes a serpentine portion in the cell that serially connects the ports and extends from a port in one surface to a port in the other surface and back to a port in the one surface, and a sensor is disposed in sealing engagement with each sensing port and forms a portion of the serpentine flow path so that sample fluid to be analyzed contacts a surface of each sensor.

In accordance with another aspect of the invention, there is provided an analysis system for measuring a parameter of a fluid sample that includes a flow-through cell which has opposed surfaces with at least one port in each surface, including an inlet port, an outlet port, and at least one sensing port. A heat sink member is on each side of the flow-through cell, each heat sink member having a surface in mating heat exchange contact with a corresponding one of the opposed cell surfaces, and temperature control structure is provided for stabilizing the temperature of the heat sink members and the cell. A sample flow path includes a portion in the cell connecting the ports, and a sensor extends through a bore in one of the heat sink members with a sensing tip disposed in sealing engagement with the sensing port and forming a portion of the flow path so that sample fluid to be analyzed contacts the tip surface of the sensor. Preferably the heat sink members are electrically grounded metal blocks with planar surfaces in mating heat exchange contact with corresponding planar opposed cell surfaces in a sandwich array.

In a particular embodiment, the flow-through cell is of transparent material so that fluid sample in a serpentine flow path may be visually observed and the serpentine flow path includes a plurality of straight passage segments, each of which extends through the cell from one surface to the other, with each passage segment extending from a port in one surface to a port in the other surface, and the passage segments at each port being disposed at an angle to one another. Each passage segment is of capillary dimension (less than one millimeter in diameter), the opposed-cell surfaces are planar and spaced less than five centimeters apart, and the volume of the serpentine flow path between the inlet and outlet ports is less than two hundred microliters.

A clear front wall member of the module is seated against the heat sink members and two chambers in that front wall member hold calibrating gas conditioning liquids—thus stabilizing the temperature of the conditioning liquids at essentially the stabilized system temperature and permitting flow rates of the calibrating gases to be adjusted by observing bubble rates in the chambers.

A fluid control in the flow-through cell has a first mode in which the sensing ports are connected in series with the inlet port so that fluid from the same sample may be flowed serially from the inlet port to the sensing ports for concurrent sensing by the sensors, and a second mode in which a first sensing port is in fluid communication with a first calibrating fluid inlet, a second sensing port is in fluid communication with a second calibrating fluid input, and the sensing ports are in fluid isolation from one another so that the sensors may be calibrated concurrently and independently of one another.

Also in that particular embodiment, a through passage in one of the heat sink blocks is in alignment with the inlet port and the sample is introduced through a sample preheater assembly in the through passage to the inlet port. A first sensor is connected to measure a gaseous parameter of the fluid sample at a first sensing port, and a second sensor is connected to measure an ionic parameter of the fluid sample at a second sensing port, and the fluid control is connected between the first and second sensing ports.

In that particular embodiment, the serpentine path in the flow-through cell extends in a generally vertical direction with the sample to be analyzed being flowed upwardly through the serpentine flow path by pump means connected to the outlet port, and a flush solution being flowed downwardly (in the reverse direction) through the serpentine flow path. A reference port in one of the cell surfaces is in communication with the serpentine path, and the serpentine path has a loop-type of trap portion for preventing reference electrolyte from flowing from the reference port to a sensing port.

The system further includes a series of sample detectors disposed at spaced points along the length of the sample path for detecting the presence of sample fluid at spaced points along that path, the sample detectors being components of a sample position sensing system of the electrical conductivity type. In one operational mode, three parameters of a 120 microliter sample are measured concurrently, and in a second operational mode parameters of a 65 microliter sample are measured serially with the sample position being monitored by the sample position detectors.

While a preferred embodiment of the invention is designed for measuring an ionic parameter and partial pressures of gases of blood and blood derivatives, the invention is not limited to blood gas measurements and may be used with other sensing systems.

Other features and advantages will be seen as the following description of a particular embodiment progresses, in conjunction with the drawings, in which.

DESCRIPTION OF PARTICULAR EMBODIMENT

Figure 1:
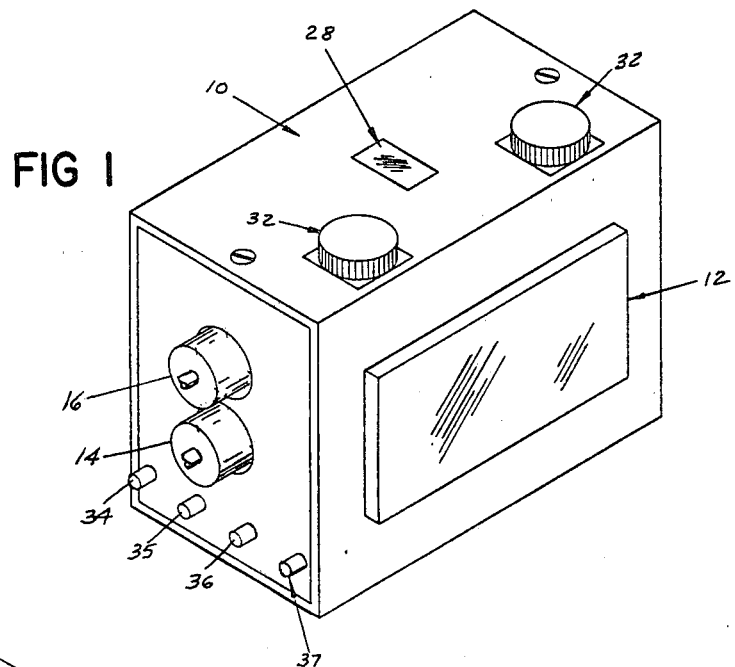
FIG. 1 is a perspective view of a blood gas analysis module in accordance with the invention.
Figure 2:
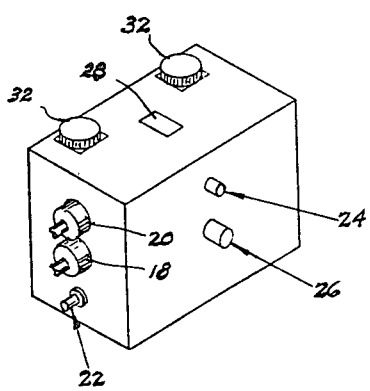
FIG. 2 is a perspective view showing the rear of the module shown in FIG. 1.

A blood gas analysis module for use in a blood gas analysis system in accordance with the invention is shown in FIG. 1. That module includes a housing 10 that has a front viewing window 12 and that receives a $pO_2$ electrode assembly 14 and a pH elctrode assembly 16 at one end. As indicated in the rear perspective view of the module in FIG. 2, the housing receives a $pCO_2$ electrode assembly 18 and a reference electrode assembly 20 at the other end. The module has a sample inlet port 22 at one end surface below carbon dioxide assembly 18 and an outlet port 24 in its rear face. A valve shaft 26 also projects from the rear face of the module. In the upper surface of the module is a window 28 for admitting light to the flow-through sample cell 30 within module 10. On either side of viewing window 12 is a chamber that is closed by a fill cap 32 and which contains water for humidifying calibration gases for calibration of each gas electrode. Ports 34, 35, 36, and 37 for connection to sources of calibration fluids are at the left end of the analysis module.

Figure 4:
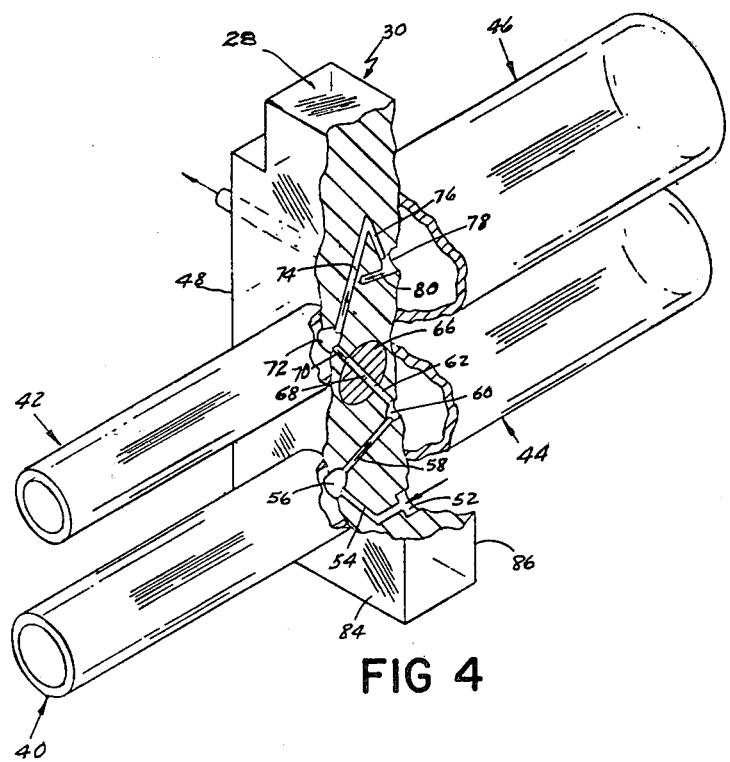
FIG. 4 is a perspective front view of a subassembly of the cell member and electrode sleeves.
Figure 3:
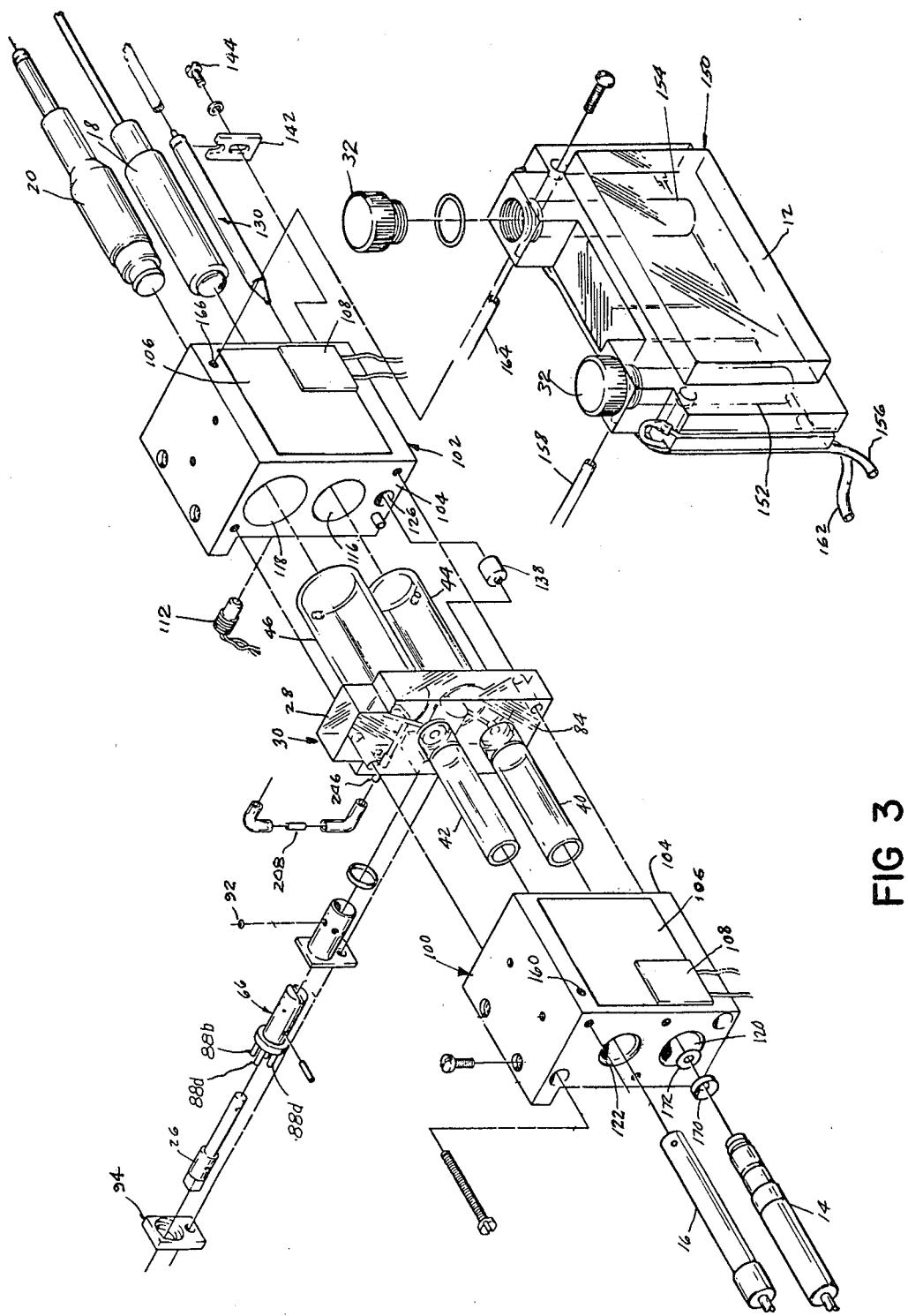
FIG. 3 is an exploded front view of components of the module of FIG. 1.
Figure 5:
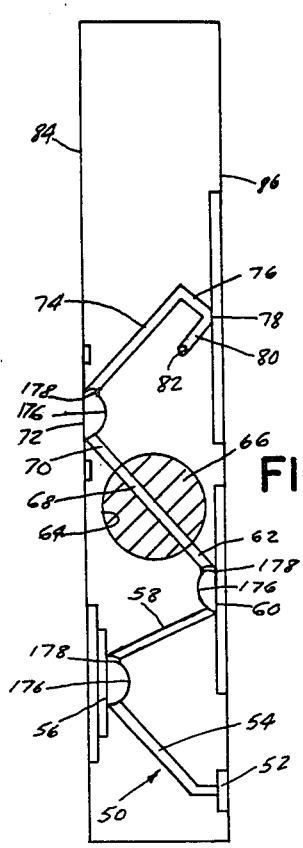
FIG. 5 is a diagrammatic sectional view showing the sample flow path through the cell member.

Further details of the analysis module may be seen with reference to FIG. 3. Flow-through cell 30 is fabricated from a clear colorless (acrylic) material and has four sleeves 40, 42, 44, 46 of the same material bonded to the cell body 30 to provide a leakproof unit. The rear surface 48 of cell body 30 has a reflective coating that in combination with the wide aperture of viewing window 12 enhances the visibility of the sample to be analyzed in the flow path 50 that extends through cell 30. As indicated in the perspective view of FIG. 4 and the diagrammatic sectional view of FIG. 5, that flow path extends from an inlet port 52 through a first passage segment 54 to a sensing port 56, through a second passage segment 58 to a second sensing port 60; through a third passage segment 62 to a chamber 64 which receives a flow control valve spool 66 that has a through passage 68; through a passage segment 70 to a third sensing port 72; through passage segments 74 and 76 to a reference port 78; and through passage segments 80 and 82 to the rear surface of cell 30. Sensing ports 56 and 72 are disposed in planar surface 84 of cell 30, and sensing ports 60 and 78 are disposed in opposed planar surface 86. The diameter of each passage segment is about 0.7 millimeter, and the volumetric displacement of the sample flow path from inlet port 52 to the exit port at the rear face of cell 30 is about 55 microliters. While various types of fluid control 66 may be utilized, a suitable fluid control is the rotary valve disclosed in copending application Ser. No. 104,296 filed Dec. 17, 1979, and entitled Spool Valve and assigned to the same assignee as this application, the disclosure of which is incorporated herein by reference. As indicated in FIG. 4, the spool 66 of the valve has a through passage 68. Also formed in the spool 66 are four calibration passages 88, two of which are shown in the sectional view of FIG. 6. Each calibration passage 88 extends to a port 90 in the cylindrical surface of spool 66. Each port 90 is sealed by a captivated O-ring 92 and retainer plate 94 is secured with fastener 96.

Figure 7:
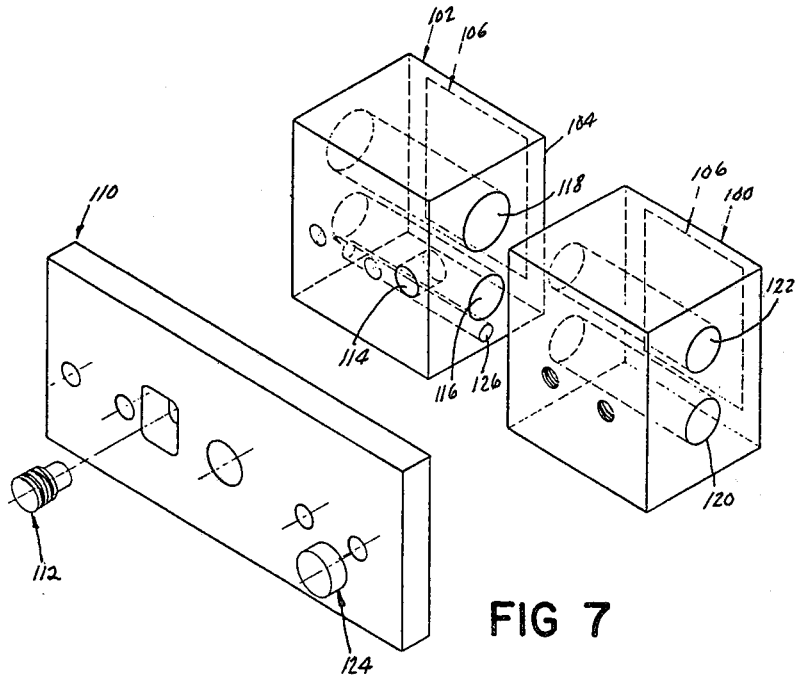
FIG. 7 is an exploded rear view of the heater blocks 100, 102 and assembly plate 110.

Referring again to FIG. 3, on either side of cell 30 is an aluminum heater block 100, 102, each of which has a planar surface 104 that is clamped in heat transfer engagement with the corresponding planar surfaces 84, 86 of cell 30. Secured to the front surface of each heater block is a heater pad 106 with a terminal connection 108. Common assembly plate 110 as indicated in FIG. 7 is bolted to the rear of heater blocks 100, 102. A temperature control probe 112 is mounted in recess 114 of block 102 between the electrode sleeve bores 116 and 118. Similar electrode sleeve bores 120 and 122 are formed in heater block 100. Heater pads 106 are wired in parallel to a proportional controller which regulates the temperature of the heater blocks 100 and 102, and thermal cutout 124 provides protection against over heating.

Figure 8:
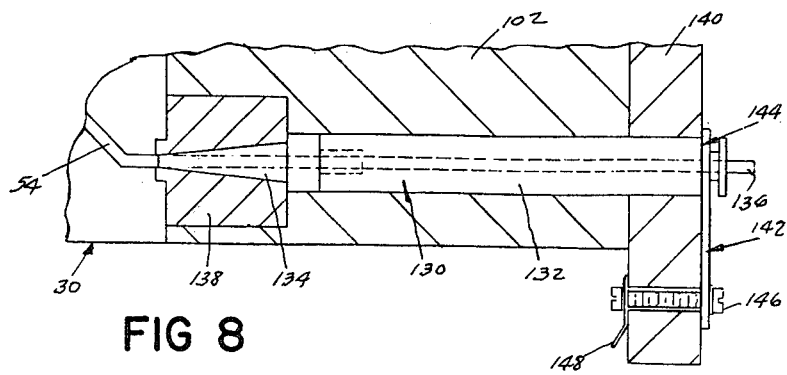
FIG. 8 is a sectional view through a heater block showing details of the sample preheater.

Disposed in bore 126 of heater block 102 (see FIG. 8) is a sample preheater 130 which includes an aluminum sleeve 132, a stainless steel taper fitting 134, and a through stainless steel tube 136. A high electrical resistance epoxy coating on outer surface of aluminum sleeve 132 isolates that sleeve from heater block 102. An elastomer seal 138 is received in heater block 102 and in turn, the tapered end of fitting 134 is seatingly sealed in elastomer seal 138. There is an insulator end plate 140 bolted to the outer end face of each heating block. Clamp plate 142 engages an uncoated surface 144 of heater sleeve 132 and provides an electrical connection through fastener 146 to sensor lead 148 as a component of the electrical conductivity sample position sensing system.

With reference once again to FIG. 3, the front wall of the module includes a clear plastic (acrylic) member 150 in which is formed viewing window 12, on either side of which is a humidifier chamber 152, 154 that is closed by cap 32. Calibration gas from inlet 37 is flowed through conduit 156 into chamber 152 and out through conduit 158 which is disposed in bore 160 of heater block 100. A second calibration gas from inlet 36 is flowed through conduit 162 to humdifier chamber 154 and out through conduit 164 which is disposed in bore 166 of heater block 102. The temperature of the humidifying water in each chamber 152, 154 is maintained at essentially the stable system temperature (as determined by the temperature of heater blocks 100 and 102) as the acrylic member 150 is seated against the front surfaces of the heater block, and the gas flow rate through each chamber may be controlled by observation of bubbles through each water reservoir 152, 154.

Figure 9:
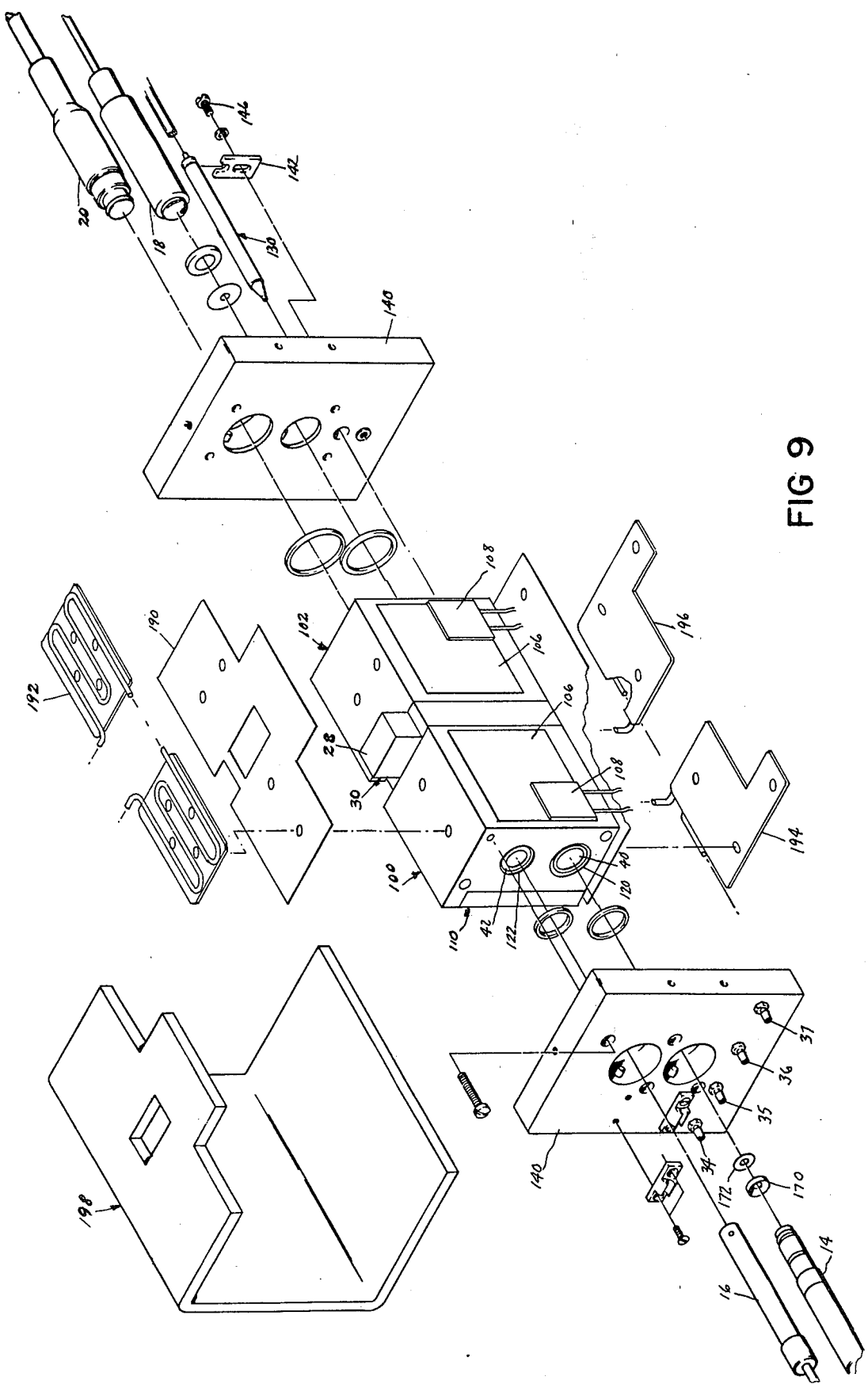
FIG. 9 is an exploded front view of components of the module of FIG. 1 with cell member 30 and heater blocks 100, 102 assembled together.
Figure 10:
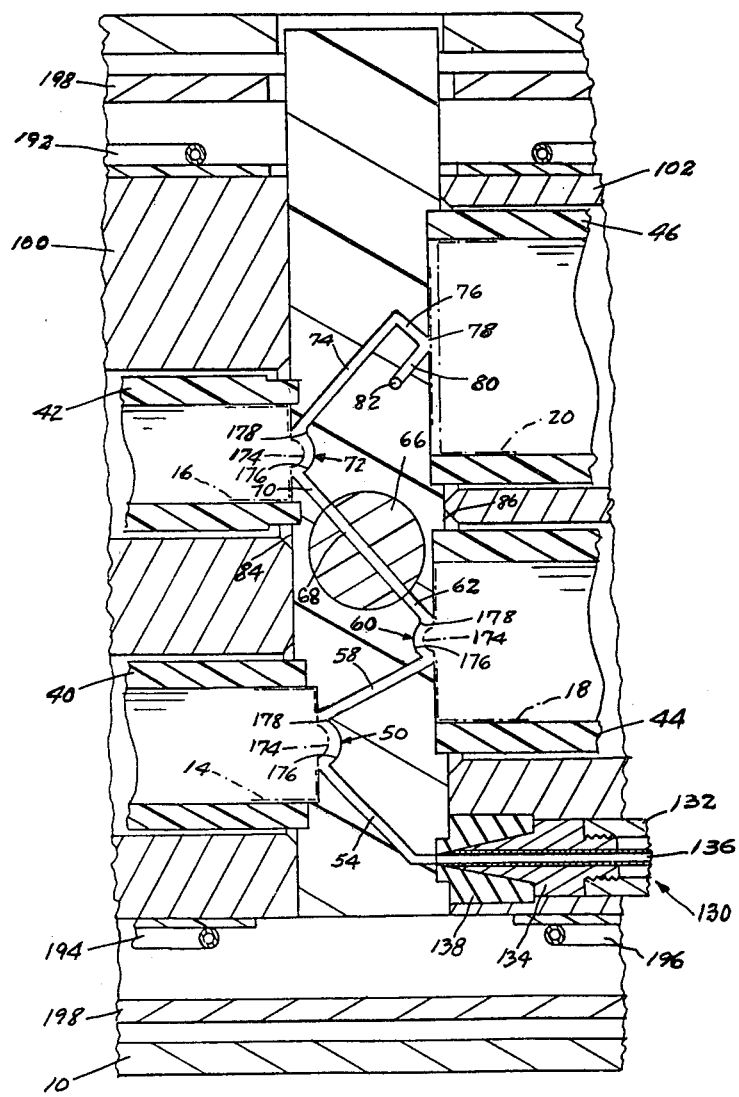
FIG. 10 is a sectional view showing the sample flow path through the cell member.

As indicated in the subassembly shown in FIG. 9, sleeves 40 and 42 are inserted through bores 120 and 122 in heater block 100, and sleeves 44 and 46 are similarly inserted through bores 116 and 118 in heater block 102. The $O_2$ electrode assembly 14 together with retainer 170 and elastomer seal 172 are inserted through sleeve 40 and seated at sensing port 56 of cell 30. $CO_2$ electrode assembly 18, pH electrode assembly 16, and reference electrode assembly 20 are similarly seated at cell ports 60, 72, and 78 respectively as indicated in FIG. 10 each bulb-type projection 174 being received in an hemispherical cavity 176 with the seal 172 sealing the cavity 176. A compression type spring axially loads each electrode to maintain the seal. Each capillary passage segment, as indicated in FIG. 10 extends to the intersection between the intersection of cavity 176 and the planar cell surface 84, 86 at an angle of about fifty degrees to surface 84, 86 so that the formation of a meniscus due to surface tension of residual fluid in cavity 176 is minimized. A groove 178 at the junction between the cavity 176 and the exit passage segment relieves entrapment of gases.

Mounted on top of the heat blocks 100, 102 on electrical insulator sheet 190 is a cleaning solution preheater 192; and similar buffer solution preheaters 194, 196 are mounted on the bottom surfaces of blocks 100 and 102, respectively. A fiberglass insulated sleeve 198 is disposed over the top, rear, and bottom walls of this subassembly and is encased in housing 10. Thus the aluminum heat sink blocks 100, 102 which are maintained at 37° C., stabilize the temperature of flow-through cell 30, gas conditioning chambers 152, 154, and preheaters 192, 194 and 196, in a module assembly that is about fifteen centimeters long, about eight centimeters high and about six centimeters deep. Blocks 100, 102 are electrically grounded and provide shielding for electrodes 14, 16, 18, and 20.

Figure 11:
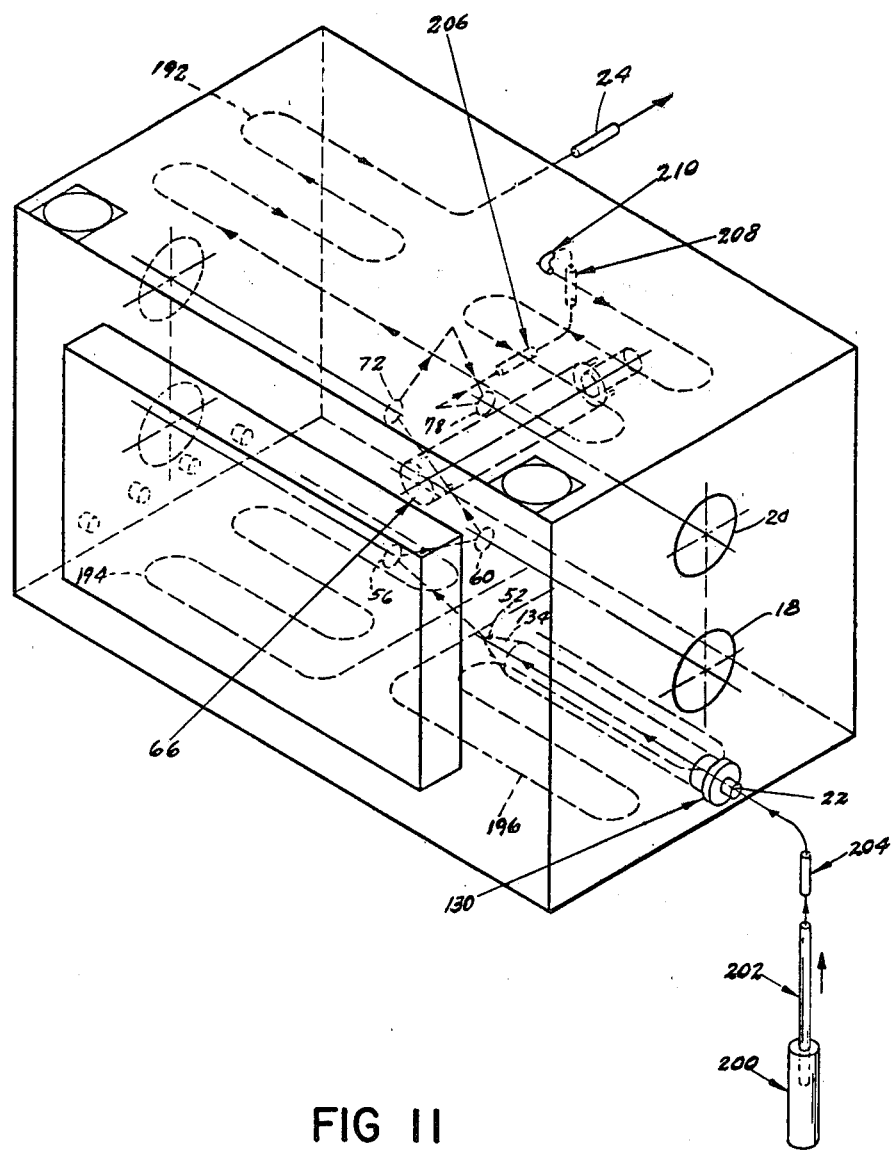
FIG. 11 is a diagrammatic view showing location of position sensors in the sample flow path in the module of FIG. 1.

The sample flow path through the module is indicated in the diagram of FIG. 11. The sample to be analyzed is withdrawn from sampling vessel 200 by sampling needle 202 and flows through a first position sensor 204 to inlet 22 of sample preheater 130. The sample emerges from tapered tip 134 of preheater 130 and flows through the serpentine path of measuring cell 30 from inlet port 52 serially past sensor port 56, sensor port 60, through valve 66, past sensor port 72 and reference port 78, through second position sensor 206 and third position sensor 208 and fourth position sensor 210 into the flush preheater 192 on top of the heater block and then out exit port 24 at the rear of the module. Position sensors 204, 206, 208, and 210 function in a position sensing system that utilizes the electrical conductivity of the sample to complete electrical circuits, in conjunction with the sample preheater 130 and the rotary valve 66. A 210 hertz signal is applied to the sample preheater 130 and to the valve 66 for sample position sensing purposes.

Figure 6:
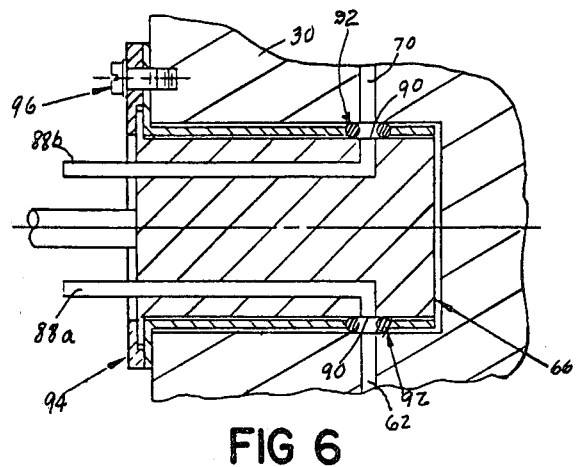
FIG. 6 is a sectional view showing the rotary spool valve 66 in a calibration position.

Flow control valve 66 has three operative positions, an analysis position in which transverse passage 68 through the valve spool is aligned with passage segments 62 and 70; a first calibrating position (as shown in FIG. 6) in which calibration gas from inlet 37 is bubbled through humidifying chamber 152 and then flowed to valve passage 88a in the spool that is connected to passage segment 62 and a buffer liquid from inlet 35 is flowed through preheater 194 and the upper inlet 88b to passage segment 70; and a second calibrating position (with spool 66 rotated through a further 60 degree angle) in which a calibration gas from inlet 36 is flowed through bubble chamber 154 and port 88c of the spool valve for flow into passage segment 62 and a buffer from inlet 34 is flowed through preheater 198 to valve inlet 88d to passage segment 70.

The sensing module has five operational modes: two calibration modes, two sample analysis modes, (a 65 microliter sample mode and a 120 microliter sample mode), and a flush mode. External microprocessor control selects the appropriate fluid flow patterns for each function.

In the 120 microliter sample analysis mode, rotary valve 66 is indexed to the sample position as shown in FIG. 11. Sampling needle 202 is inserted in sampling vessel 200 and the peristaltic pump connected to exit port 24 is operated to induct about 120 microliters of blood up to preheater 130. The conductivity of the blood sample completes a circuit between the preheater 130 and sampling needle 206, signaling the induction of the sample, and the pump is stopped to allow withdrawal of needle 202 from vessel 200. The pump then advances the sample to valve 66, and the pump is stopped to allow equilibration of the oxygen electrode 14 and the carbon dioxide electrode 18. The pump then advances the 120 microliter sample to sensor 210. After the blood sample to be analyzed has been so flowed and located concurrently at the three sensor ports and the reference port, data translating circuits are released and measurements of pH, $pCO_2$, and $pO_2$ are simultaneously obtained.

Figure 12:
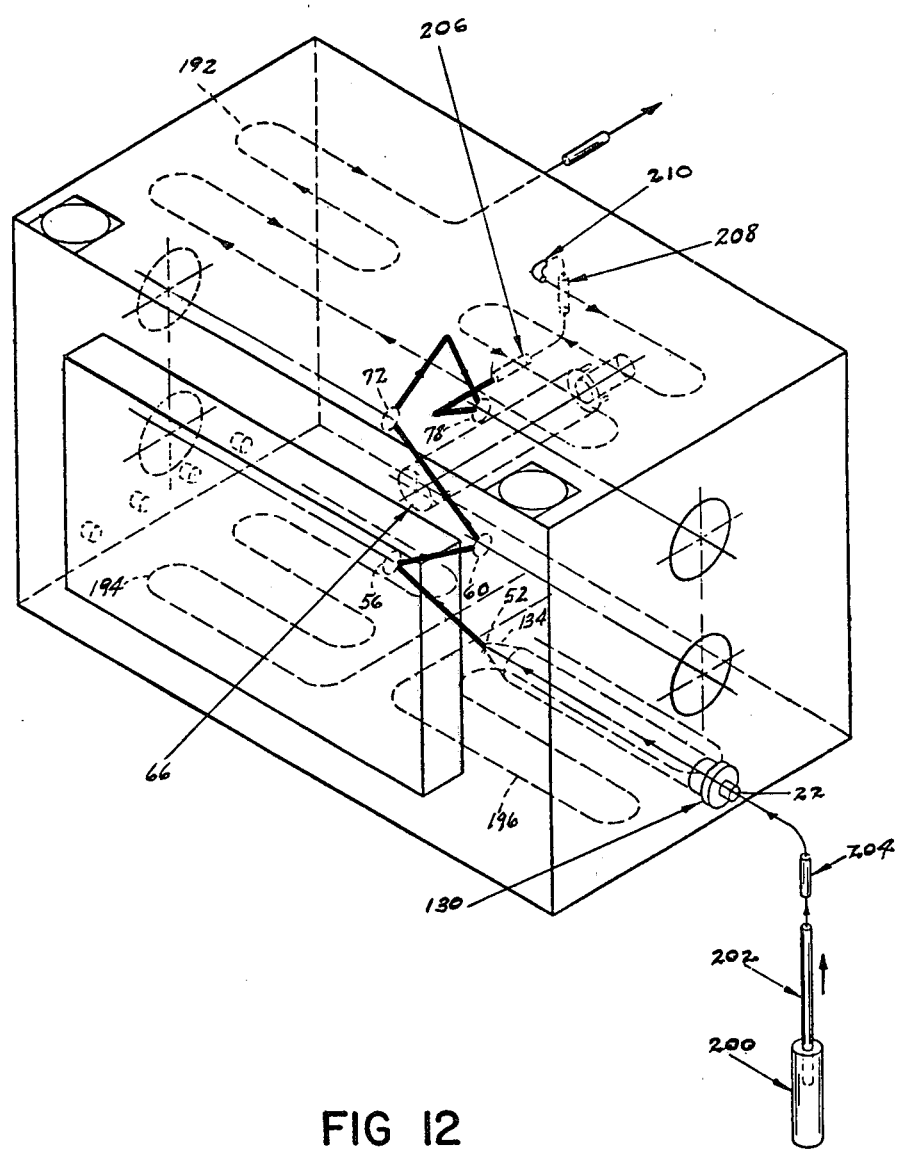
FIGS. 12 and 13 are diagrammatic views similar to FIG. 11 showing two locations of a smaller sample (65 microliter volume) for analysis.
Figure 13:
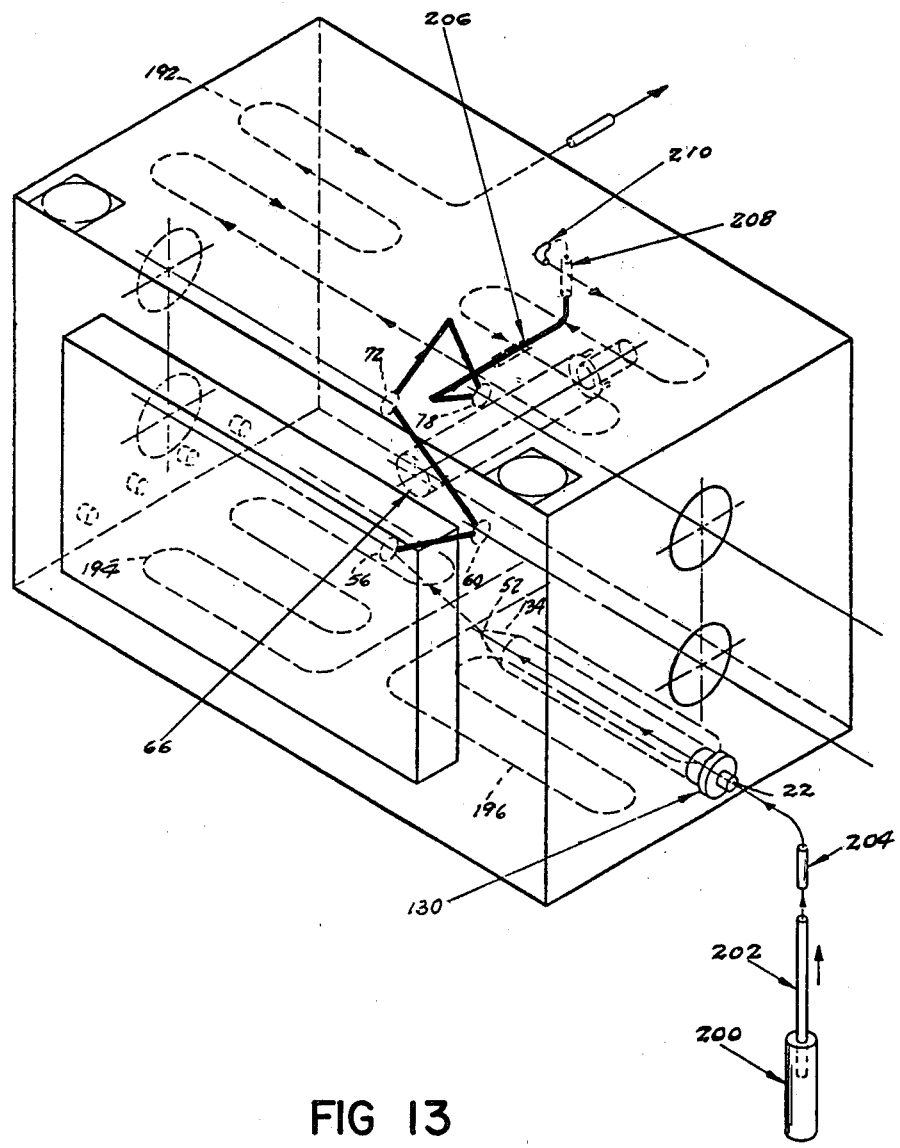

When it is desired to analyze a smaller (65 microliter) sample volume, the sample to be analyzed is inducted only to sensor 204 and then the sampling needle is withdrawn from the sampling vessel. The sample is first advanced through preheater 130 to the sensor 206 (FIG. 12) where there is a pause for equilibration of the carbon dioxide and pH electrodes. At this time the data translating circuit for the oxygen electrode 14 is released and a $pO_2$ measurement on the microsample is made. The sample is then advanced to sensor 208 (to the position shown in FIG. 13) and pH and carbon dioxide measurements are made. After the measurements have been completed, the sample is flushed from the module.

Figure 14:
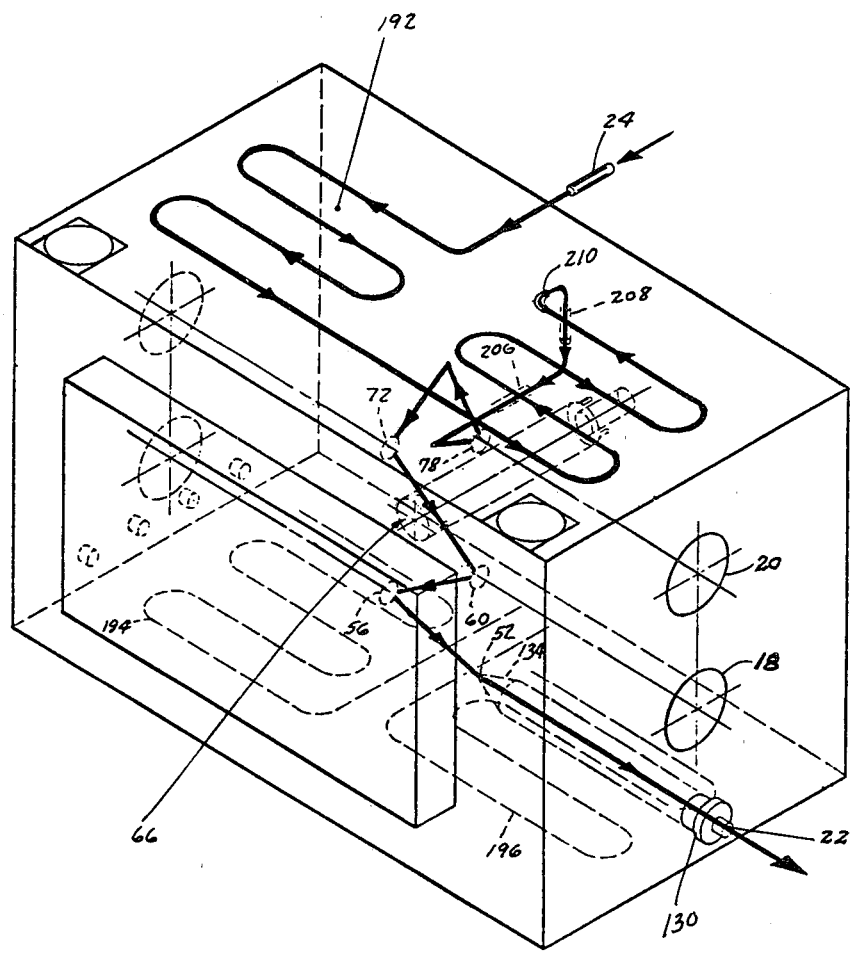
FIG. 14 is a diagram similar to FIG. 11 showing the flush flow path.

The flush cycle flow path is shown in FIG. 14. In the flush cycle, flow control valve 66 remains in the sample position, and cleaning is accomplished by back flushing the system under pressure with flush solution being pumped through flush preheater 192 and the serpentine passage in cell 30 and through preheater 130 and the sampling needle 202 to waste along the path as indicated in FIG. 14.

Figure 15:
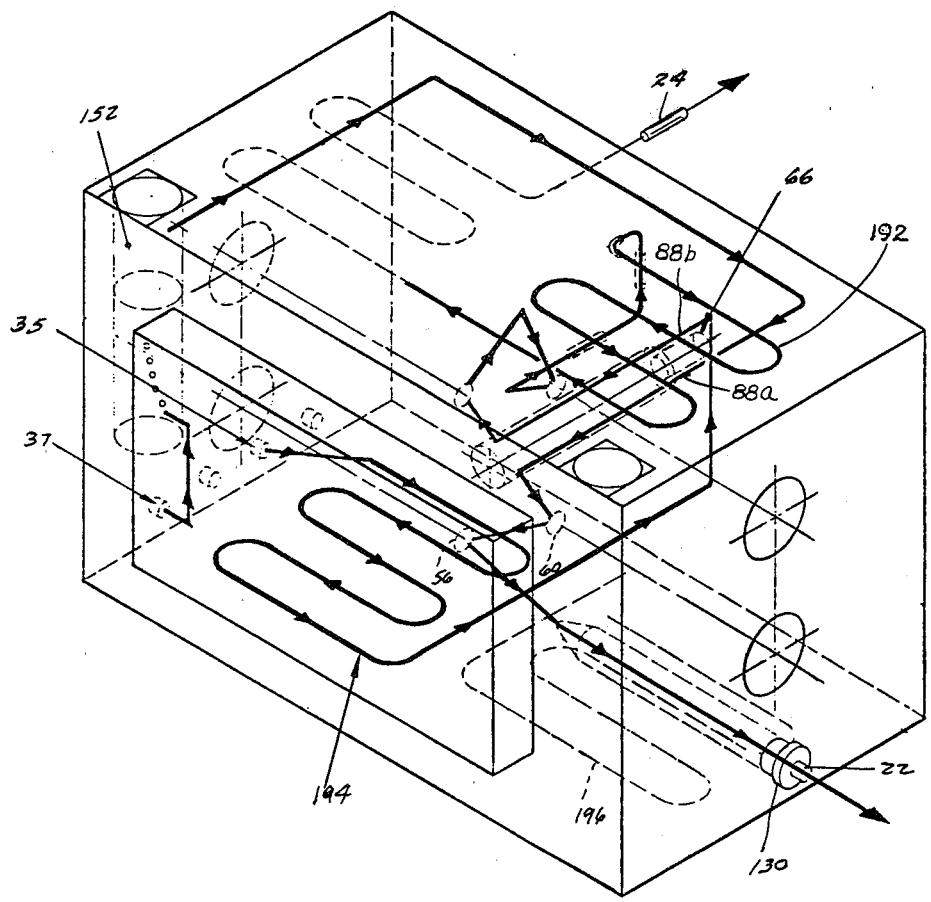
FIG. 15 is a diagram similar to FIG. 11 showing the flow path of calibration fluids in one of the calibration modes.

The flow path in a calibration mode indicated in FIG. 15. For calibration, rotary valve 66 is indexed (rotated 60 degrees) to a first calibration position and then indexed a further 60 degrees to a second calibration position. In each calibration position, a calibration gas bubble chamber is connected to an inlet of valve 66 and the calibration gas is humidified by bubbling through the bubble chamber and then flows through the valve into passage segment 62 and past sensor ports 60 and 56 and out sample preheater. At the same time a buffer solution is pumped by the aspiration pump connected to the exit port 24 through the selected buffer preheater and valve passage to passage segment 70 for flow past sensing port 72 and reference port 78.

While a particular embodiment of the invention has been shown and described, various modifications will be apparent to those skilled in the art, and therefore it is not intended that the invention be limited to the disclosed embodiment or to details thereof and departures may be made therefrom within the spirit and scope of the invention.

What is claimed is:

1. An analysis system for measuring a parameter of a fluid sample comprising:
   two metal heat sink members,
   a flow-through cell disposed between said heat sink members, said flow through cell having parallel opposed surfaces and each of said heat sink members having a surface in rating heat exchange contact with a corresponding one of said opposed cell surfaces,
   structure in said cell defining an inlet port, an outlet port, means defining a port capable of accepting a sensor, and means defining a flow path that serially connects said inlet port to said sensor accepting port and said sensor accepting port to said outlet port,
   a bore in one of said heat sink members,
   sample analysis electrode structure that has a sensor portion at one end thereof, said sample analysis electrode structure extending through said bore with said sensor portion disposed in sealing engagement in said sensor accepting port and forming a portion of the flow path so that sample material in said flow path contacts said sensor portion of said electrode structure,
   heater structure in physical contact with each said heat sink member,
   a temperature sensor in one of said heat sink members for sensing the temperature of said one heat sink member,
   preheater flow-through structure disposed in one of said heat sink members and connected to said inlet port for heating sample material being flowed to said flow-through cell for analysis, and
   flush solution flow-through structure physically supported in heat exchange relation with said heat sink members and connected to said outlet port path for stabilizing the temperature of flush solution to be flowed through said sample flow path.

2. The system of claim 1 wherein said flow-through cell includes means defining at least one sensor accepting port in each of said surfaces, each said cavity being capable of accepting one end of a sensor and said sample flow path defining means in said flow-through cell defines a serpentine portion that extends from said inlet port to a sensor accepting port in one surface, then to a sensor accepting port in the opposite surface and then to said outlet port.

3. The system of claim 2 wherein said serpentine portion defining means includes a plurality of straight passage segments, where each said passage segment extends through said cell from one said surface to the other said surface, with each passage segment extending from a port in said one surface to a port in said other surface, the passage segments at each port being disposed at an angle to one another.

4. The system of claim 3 wherein each said passage segment is of capillary dimension (less than one millimeter in diameter), said opposed cell surfaces are planar and spaced less than five centimeters apart.

5. The system of either claim 4 or 1 wherein the volume of said flow path between said inlet and outlet ports is less than two hundred microliters.

6. The system of either claim 2 or 4 wherein said serpentine flow path in said flow-through cell extends in a generally vertical direction and further including means to flow the sample to be analyzed upwardly through said serpentine flow path.

7. The system of claim 6 wherein said sample flow means includes pump means connected to said outlet port, and further including means to flow a flush solution downwardly through said serpentine flow path.

8. The system of claim 7 and further including a reference port in one of said cell surfaces in communication with said serpentine path, said serpentine path having a trap portion for preventing reference electrolyte from flowing from said reference port downwardly to a sensing port.

9. The system of either claim 2 or 4 wherein said flow-through cell includes an annular sealing surface surrounding each said sensor port and a surface of said serpentine flow path intersects said annular sealing surface.

10. The system of claim 9 wherein one of said electrode structures includes a protruding tip, and said flow-through cell includes a recess at one of said sensor accepting ports in fluid communication with said serpentine sample flow path for receiving said protruding tip so that the sample fluid to be analyzed contacts and flows around said protruding tip.

11. The system of either claim 1 or 4 wherein said flow-through cell is of transparent material so that fluid sample in said flow path may be visually observed, and further including housing structure with a transparent front wall portion that includes window structure for viewing said flow-through cell, and said transparent front wall portion includes chamber structure for storing conditioning liquid through which a sensor calibrating gas is bubbled.

12. The system of claim 2 and further including structure in said cell defining a reference port in one of said cell surfaces in communication with said serpentine portion of said flow path defining means, said serpentine portion having a trap portion for preventing reference electrolyte from flowing from said reference port to a sensor accepting port.

13. The system of either claim 1 or 12 wherein said flow-through cell is of transparent material so that fluid sample in said flow path may be visually observed.

14. The system of claim 13 wherein said system includes a light transmitting window in the front wall of the housing for transmitting light to said flow-through cell.

15. The system of either claim 2 and further including a series of sample detectors disposed at spaced points along the length of said serpentine path for detecting the presence of sample fluid at spaced points along said path.

16. The system of claim 15 wherein said plurality of sample detectors are components of a sample position sensing system of the electrical conductivity type.

17. The system of claim 2 and further including means defining first and second calibrating fluid inlets, and fluid control means in said serpentine portion in said cell, said fluid control means having a first mode in which said sensor accepting ports are connected in series with said inlet port so that fluid from the same sample may be flowed serially from said inlet port to said sensor accepting ports for concurrent sensing by said sensors, and a second mode in which a first sensor accepting port is in fluid communication with said first calibrating fluid inlet, a second sensor accepting port is in fluid communication with said second calibrating fluid inlet, and said sensor accepting ports are in fluid isolation from one another so that said sensors may be calibrated concurrently and independently of one another.

18. The system of claim 1 and further including means defining a second port capable of accepting a sensor, a second sample analysis electrode structure having a sensor portion in sealing engagement with said second sensor accepting port, said first electrode structure being connected to measure a gaseous parameter of the fluid sample at said first sensor accepting port, and said second electrode structure being connected to measure an ionic parameter of the fluid sample at said second sensor accepting port, said flow path defining means serially connecting said inlet port to said first sensor accepting port, said first sensor accepting port to said second sensor accepting port and said second sensor accepting port to said outlet port, and a fluid control connected in said flow path defining means between said first and second sensor accepting ports.

* * * * *